US005866539A

United States Patent [19]
Blackburn et al.

[11] Patent Number: 5,866,539
[45] Date of Patent: Feb. 2, 1999

[54] METHOD FOR THE CONTROL OF ANTIBIOTIC-RESISTANT GRAM POSITIVE BACTERIA AND TREATMENT OF INFECTION

[75] Inventors: Peter Blackburn, New York; Beth P. Goldstein, Tarrytown, both of N.Y.

[73] Assignee: AMBI Inc., Tarrytown, N.Y.

[21] Appl. No.: 667,650

[22] Filed: Jun. 21, 1996

Related U.S. Application Data

[60] Provisional application No. 60/000,435 Jun. 23, 1995.
[51] Int. Cl. [6] .................................................. A61K 38/16
[52] U.S. Cl. .................................... 514/9; 514/12; 514/13
[58] Field of Search .................................. 514/9, 11, 12, 514/13; 530/317, 324, 325, 326, 825

[56] References Cited

U.S. PATENT DOCUMENTS

| | | | |
|---|---|---|---|
| 4,931,390 | 6/1990 | Recsei | 435/69.1 |
| 4,980,163 | 12/1990 | Blackburn et al. | 424/94.63 |
| 5,217,950 | 6/1993 | Blackburn et al. | 514/2 |
| 5,260,271 | 11/1993 | Blackburn et al. | 514/2 |
| 5,334,582 | 8/1994 | Blackburn et al. | 514/2 |
| 5,512,269 | 4/1996 | Molinay Vedia et al. | 424/45 |

FOREIGN PATENT DOCUMENTS

| | | |
|---|---|---|
| 9428726 | 12/1994 | WIPO . |
| WO 9428726 | 12/1994 | WIPO . |

OTHER PUBLICATIONS

Brotz et al. "Mode of Action of the Lantibiotic Mersacidin: Inhibition of Peptidoglycan Biosynthesis . . . " Antimicrob. Agents Chemotherapy. 39 (3): 714–719, 1995. (abstract only).

Barrett et al. "In Vitro Activity of Mersacidin (M87–1551), . . . " Diagn. Microbiol. Infect. Dis. 15(7): 641–644, 1992. (abstract only).

Murray, B.E. "The Life and Times of Enterococcus" Clin. Microbiol. Rev. 3(1): 46–65, 1990. (abstract only).

"Invasive Group A Streptococcal Infections—United Kingdom, 1994" MMWR, pp. 401–402, 1994.

Bavin et al. "Nisin in Experimental Tuberculosis." Lancet 1:127–129, 1952.

Gowans et al. "Some Properties of Nisin." Brit. J. Pharmacol. 7:438–449, 1952.

Chatterjee et al. "Mersacidin, a New Antibiotic From Bacillus. In vitro and in vivo antibacterial activity." J. Antibiot. (Japan), 45(6):839–845, 1992. (abstract only).

Szybalski, W. "Genetic Studies in Microbial Cross Resistance to Toxic Agents," Dept. Health and Human Services, FDA Fed. Regis. 53(66):pp. 1095–1103, 1988. (odd–numbered pages only).

Hirsch et al. "Some Recent Applications of Nisin." Lancet, ii:190–193, 1949.

Mattick et al. "Further Observations on an Inhibitory Substance (nisin) from *Lactic Streptococci*" Lancet 2:5–8, 1947.

Somma et al. "Gardimycin, a New Antibiotic Inhibiting Peptidoglycan Synthesis" Antimicrob. Ag. Chemother. 11:396–401, 1997.

Arioli et al. "Gardimycin, a New Antibiotic from Actinoplanes" J. Antibiot. 29:511–515, 1976.

Karchmer, A.W. "*Staphylococcus Aureus* and Vancomycin: The Sequel" Ann. Int. Med. 115(9):739–741, 1991.

Jung et al. "Nisin and Novel Lanibiotics" ESCOM Science Publishers, Leiden, pp. 1–34, 1991.

Emori et al. "An Overview of Nosocomial Infections, . . . " Clin. Microbiol. Rev. 6(4):428–442, 1993.

Ramseier, H.R. "Die Wirkung von nisin auf *closridium butyricum* Prazm." Archiv. fur Mikrobiol. 37:57–94, 1960.

Hossack et al. "The Effects of Nisin on the Sensitivity of a Range of Microorganisms to Antibiotics. . . " Federal Register, vol. 53, No. 668, pp. 1–30, Apr. 6, 1988.

Stutman, H.R. "Penicillin–resistant *Streptococcus Pneumoniae*. . . " Infections in Medicine 10: Suppl. D.:51–55, 1993.

Thornsberry et al. "Increasing Penicillin Resistance in *Streptococcus Pneumoniae* in the U.S. . . . " Infections in Medicine 10 Suppl. D.:15–24, 1993.

Reisinger et al. "The Effect of Nisin on Murein Synthesis" Arch. Microbiol. 127:187–193, 1980.

Nobel et al. "Co–transfer of Vancomycin and Other Resistance Genes . . . " FEMS Microbiol. Lett. 93:195–198, 1992.

Sahl, H. –G., et al., *Eur. J. Biochem.* 230,827–853 (1995).

Jung, G., Lantibiotics: A Survey, In: Nisin and Novel Lantibiotics, Jung, G. and Sahl, H. –G., eds., ESCOM Science Publishers, Leiden, pp. 1–34 (1991).

Szybalski, W., Antibiotics and Chemotherapy 3, 1095–1103 (1953).

Goldstein, B.P., "Tuberculosis in the 1990s," La Chimica e l'Industria 76, 196–198 (1994).

Cole, S.T. Trends in Microbiology 2, 411–415 (1994).

Orberg et al. Survey of Antimicrobial Resistance in *Lactic Streptococci*. Applied and Environmental Microbiology, Mar. 1985, vol. 49, No. 3, pp. 538–542.

*Primary Examiner*—Jeffrey E. Russel
*Attorney, Agent, or Firm*—White & Case L.L.P.

[57] ABSTRACT

The invention concerns methods for killing antibiotic-resistant pathogenic bacteria responsible for disease in humans and animals. The methods employ a lanthocin such as nisin as bactericidal agent.

2 Claims, No Drawings

METHOD FOR THE CONTROL OF ANTIBIOTIC-RESISTANT GRAM POSITIVE BACTERIA AND TREATMENT OF INFECTION

BACKGROUND OF THE INVENTION

This application claims the benefit of U.S. Provisional Application No. 60/000,435, filed Jun. 23, 1995.

Nisin is a bacteriocin, an antimicrobial substance produced by a food grade organism and is a member of a group of similar substances referred to as lantibiotics (or lanthocins herein) and which, among others, include subtilin, epidermin, gallidermin, pep 5, cinnamycin, duramycin and ancovenin.

Nisin is produced by Lactococcus lactis subsp. lactis belonging to the Lancefield serological group. N [Mattick, A. T. R. and A. Hirsch, 1947 Lancet. 2, 5]. Nisin is a peptide comprised of 34 amino acid residues and contains five ring structures cross linked by thioether bridges that form lanthionine or β-methyllanthionine. These thioethers result from the condensation of cysteine sulfhydryl groups with dehydro side chains formed from either serine or threonine residues as a result of posttranslational modifications of a nisin precursor peptide.

It has been reported that nisin acts as a cationic surface active agent and that its activity can be neutralized by anionic detergents [Ramseier, H. R. 1960 Arch. Mikrobiol, 37, 57], and at a molecular level that nisin acts at the cytoplasmic membrane and inhibits peptidoglycan biosynthesis [Reisinger et al. 1980 Arch. Microbiol. 127, 187]. The action of nisin against vegetative bacteria is most likely the result of voltage dependent depolarization of the plasma membrane following insertion of the peptide into the lipid bilayer, possibly through the interaction of adjacent nisin molecules to form a transient pore or channel. The molecular properties of nisin and the mechanism of its biosynthesis have been the subject of extensive recent reviews [Jung, G. and H. -G. Sahl 1991 Nisin and Novel Lantibiotics ESCOM Science Publishers, Leiden].

Nisin is considered to have a narrow spectrum of activity and generally is only active against certain Gram positive bacteria, except when combined with a chelating agent when nisin is surprisingly active against Gram negative bacteria and exhibits enhanced activity against Gram positive bacteria (U.S. Pat. Nos. 5,135,910; 5,217,950; and 5,260,271 to Blackburn, et al.). Nisin has been used as an antimicrobial food preservative and is accepted as safe by JEFCA and various national authorities regulating the use of food additives including those of the USA, UK and EEC.

SUMMARY OF THE INVENTION

The invention concerns methods for preventing and treating diseases attributable to infection by antibiotic-resistant pathogens. The methods employ nisin and other lanthionine-containing bacteriocins (lanthocins), as well as structural variants thereof produced by genetic engineering or semi-synthetic chemistry. The inventive methods may suitably be used, among others, against antibiotic-resistant strains of the genera Staphylococcus, Streptococcus and Enterococcus.

DETAILED DESCRIPTION OF THE INVENTION

Bacterial infections, particularly those acquired in hospitals have become more difficult to treat, in part as the result of the selection of clinical isolates resistant to those antibiotics currently used for therapy. In particular, methicillin-resistant Staphylococcus aureus (MRSA) and methicillin-resistant coagulase-negative staphylococci (MRSE) have become resistant to most antibiotics currently available with the exception of the glycopeptide antibiotics, vancomycin and teicoplanin. Although vancomycin is the drug of choice for these infections, vancomycin is not always clinically effective [Karchmer, A. W. 1991 Annals of Internal Medicine 115: 739]. Enterococcal infections have traditionally been difficult to treat, in part because they are intrinsically resistant to many antibacterial agents, and in part, because of their tolerance (refractoriness to killing) to agents which are normally bactericidal for other bacterial species [Murray, B. E. 1990 Clin. Microbio. Rev. 3: 46]. Recently, enterococci have acquired resistance to vancomycin, and infections by vancomycin-resistant isolates of enterococci are increasing at alarming rates especially in intensive care units [Emori, T. G. and R. P. Gaynes 1993 Clin. Microbio. Rev. 6: 428]. Conjugative transfer of genetic information between enterococci and staphylococci is possible, and transfer of vancomycin-resistance has occurred in the laboratory [Noble, W. C., et al 1992 FEMS Microbiol. Lett. 72: 195]; it therefore appears to be only a matter of time before vancomycin-resistant staphylococci will emerge among hospital acquired infections. Among community-acquired infections, emerging resistance among streptococci is a cause for concern, in particular, among the pneumococci [Thornsberry, C., et al 1993 Infections in Medicine 10 Suppl. D: 15; Stutman, H. R. 1993 Infections in Medicine 10 Suppl. D: 51]. Highly toxigenic strains of Group A streptococci [Anonymous 1994 Morbidity Mortality Weekly Report 43: 401] and staphylococci (responsible for problems like necrotizing fasciitis and toxic shock-like syndromes) are difficult to treat and frequently result in the rapid demise of the patient. It is clear that new more effective and more rapidly acting antimicrobial agents are needed to combat these infections.

Although, in principle, nisin might be considered for use in certain situations wherein antimicrobials are called for and the bacteriocin was shown to be effective in preliminary animal model studies [Mattick, A. T. R. and A. Hirsch, 1947 Lancet. 2, 5; Bavin, E. M., et al 1952 Lancet 1: 127; Gowans, J. L., et al 1952 Brit. J. Pharmacol. 7: 438; Hirsch, A. and A. T. R. Mattick 1949 Lancet ii: 190], nisin was found to be insufficiently useful to be developed therapeutically in human or veterinary medicine. Actagardine and mersacidin are more recent lanthionine-containing antimicrobial peptides that have been evaluated, but found to have only moderate activity towards staphylococci and enterococci as compared to currently used therapeutic agents [Arioli, V., et al 1976 J. Antibiotics 29: 511; Somma, S., et al 1977 Antimicrob. Ag. Chemother; Barrett, M. S., et al 1992 Diagn. Microbiol. Infect. Dis. 15: 641], and are unlikely to be of therapeutic value.

However, we have found that nisin is a potent bactericidal agent against pathogenic strains of Gram positive bacteria. In particular, we have found nisin is bactericidal towards contemporary isolates of multidrug-resistant Staphylococcus aureus, methicillin-resistant coagulase-negative staphylococci, a necrotizing strain of Group A streptococci, and multidrug-resistant pneumococci. Moreover, we have found that nisin is an effective bactericidal agent for enterococci, including vancomycin-resistant enterococci. Since enterococci are notoriously refractory to antimicrobial agents, this observation is surprising, and strongly suggests that nisin may have unusual therapeutic value. Since it is accepted that the widespread use of broad spectrum antimicrobials, particularly when administered orally and in low doses, has led to the massive emergence of multidrug-resistant pathogens, it is therefore surprising, since nisin is ingested in low doses in food, that nisin-resistance and cross-resistance to other antimicrobial agents has not emerged. Although during nisin's early development as an antimicrobial food preservative, it was found not to select for cross-resistance to a range of then contemporary antibiotics [Hossack, D, J. N. Apr. 6, 1988 Federal Register Vol. 53, No. 66; Szybalski, W. Apr. 6, 1988 Federal Register Vol. 53, No. 66], the activity of nisin towards contemporary multidrug-resistant pathogens after the many years of its uncontrolled use in foods has not been evaluated until now.

These findings demonstrate that not only nisin, but other related members of this class of lanthocin antimicrobial peptides, including subtilin; epidermin; gallidermin; pep 5; cinnamycin; duramycin and ancovenin, as well as structural variants of these molecules produced by genetic engineering or by semisynthetic chemistry, should be useful in the prevention or therapy of infections caused by antibiotic-resistant bacteria in humans and animals.

Effective pharmaceutical formulations of these peptides include simple aqueous solutions suitable for parenteral delivery of the active agent via intravenous (i.v), intramuscular (i.m.), subcutaneous (s.c.), or intraperitoneal (i.p.) routes so as to permit blood and tissue levels in excess of the minimal inhibitory concentration (MIC) of the active agent to be attained and thus to effect a reduction in bacterial titers in order to prevent, treat, cure or alleviate an infection. It is anticipated that the lanthocin antimicrobial agent could be co-administered, at the same time or consecutively, with other antimicrobial agents so as to more effectively provide for a broader spectrum therapy, especially useful, in the absence of a specific diagnosis prior to initiating therapy. It is anticipated that a dosage range from about 2–200 mg/kg/day would provide effective reduction of bacterial titers.

It is also anticipated that pharmaceutical formulations suitable for topical application to skin and/or mucosal membranes, such as aqueous or petroleum-based ointments, lotions, emulsions or gels will be useful for control of antibiotic-resistant organisms. For example, a lanthocin-based topical formulation, suitable for administration to the anterior nares, of concentrations of the active agent in excess of its MIC, and thereby sufficient to reduce bacterial titers, can be expected to be particularly useful for the control of MRSA colonization in patients and healthcare personnel to thereby reduce the risk of acquiring a potentially life-threatening, antibiotic-resistant infection.

EXAMPLES

Bacterial strains. Methicillin-resistant *Staphylococcus aureus* (MRSA) and *Staphylococcus epidermidis* (MRSE) were clinical isolates provided by different European hospitals while the highly toxigenic *Streptococcus pyogenes* strain and the vancomycin-resistant *Enterococcus faecalis* strains were U.S. clinical isolates. Additional tested samples of MRSA, MRSE and of vancomycin-resistant *Enterococcus faecium* were U.S. clinical isolates. In a separate set of experiments MRSA strains from 4 different countries, MRSE strains from Spain, penicillin-resistant *Streptococcus pneumoniae* strains from 6 different countries and vancomycin-resistant enterococci from two New York hospitals were tested. Still other isolates tested came from culture collections.

Minimal inhibitory concentration (MIC). MIC were determined essentially using NCCLS (National Committee on Clinical Laboratory Standards) broth microdilution methodology. In the experiments with U.S. clinical isolates of the MRSA and MRSE and vancomycin-resistant *Enterococcus-faecium*, unsupplemented Mueller-Hinton broth was used. In the experiments with the MRSA and MRSE isolates from different European hospitals and the U.S. clinical isolates of *Streptococcus pyogenes* and vancomycin-resistant *Enterococcus faecalis,* Tryptic Soy broth was used. In the latter tests, 0.02% bovine serum albumin (final concentration 0.01%) was used in the diluent to prevent sticking of nisin to plastic microtiter wells.

Minimal bactericidal concentration (MBC). After determination of MICs, wells showing no growth were sampled and plated for colony counts. The MBC was defined as the lowest concentration at which 99.9% of the initial inoculum was killed within 24 h of contact.

Lysis of bacterial cultures and rapid bactericidal activity. Media used included 'C+Y' broth for *S. pneumoniae*, Tryptic Soy broth for staphylococci and Brain Heart Infusion broth for enterococci. Different bacterial species were incubated at 37° C. for different periods of time with different fixed concentrations of nisin, as indicated in the tables following. Lysis was measured as percent decrease in the optical density at 600 nm relative to that of the culture before exposure to nisin. In addition, in some experiments samples were removed and viable counts were determined essentially as described above under MBC.

Mouse i.p. infection model. *Staphylococcus aureus* NCTC 8325 was grown in veal infusion broth, and mice were infected intraperitoneally with $10^3$ colony-forming units (CFU) each, diluted in broth +10% (w/v) Difco bacteriological mucin. Groups of 5 mice each received either no treatment or 10 mg/kg of nisin, given intravenously (via the tail vein in 0.5 ml aqueous solution adjusted to pH 5.0) within 10 minutes after infection. The mice were observed for 48 hours in order to record deaths or adverse signs.

Example 1. Determination of the MIC and MBC of nisin against contemporary multidrug-resistant pathogens.

As shown in Table 1, nisin showed excellent inhibitory activity (MIC) against both laboratory ATCC strains and clinical isolates of different species of staphylococci, enterococci and streptococci, while Gram-negative bacteria (*Escherichia coli* and *Pseudomonas aeruginosa*) were considerably less susceptible. The clinical isolates included methicillin-resistant *Staphylococcus aureus* (MRSA) and *Staphylococcus epidennidis* (MRSE), mupirocin-resistant (mup-r) *S. aureus* and MRSA, and vancomycin-resistant (van-r) *Enterococcus-faecalis* and *Enterococcus faecium*. For all organisms tested, the MBC (that concentration killing at least 99.9% of the bacteria within 24 hours) was equal to or, in a few cases, twice the MIC, indicating that nisin is highly bactericidal for these bacteria. The observation that nisin is bactericidal for the enterococci, including vancomycin-resistant strains, is unexpected because enterococci are refractory to the bactericidal activity of most antibacterial agents.

Example 2. Determination of the bactericidal activity of nisin for multidrug-resistant pathogens.

The observations of Example 1 were confirmed and extended in additional experiments in which a large number of multidrug-resistant clinical isolates of staphylococci and enterococci, as well as multidrug-resistant pneumococci, were exposed to fixed concentrations of nisin for periods of time ranging from 20 min to 240 min. At the end of these short exposure periods, two parameters were measured: cell survival (in one set of experiments) and cell lysis (in both sets of experiments). As shown in Table 2, most of the isolates showed greater than 50% lysis measured by decrease in turbidity of the culture at 600 nm; many of the remaining strains showed measurable lysis but less than 50%. In addition, samples of nisin-treated isolates were evaluated for viability as also shown in Table 2. It was observed that percent reduction in viable counts exceeded the percent reduction in turbidity, and some isolates which exhibited comparatively little reduction in turbidity, nevertheless, showed significant reduction in viability. Thus, the bactericidal action of nisin against these bacteria does not require cell lysis, rather lysis is thought to be a late event in the reaction of bacteria to the agent. All but two isolates (both were pneumococci exposed to a low concentration for a short time) were extensively killed during the brief exposure periods of the experiments. The rapid bactericidal action of nisin towards all of the enterococcal isolates (≧99% within 4 hours) is indeed a remarkable result for these organisms.

Example 3. The efficacy of nisin towards intraperitoneal *Staphylococcus aureus* infection in mice.

The efficacy of nisin against infection was demonstrated in a mouse infection model. In this model, intraperitoneal infection leads to death of untreated animals within 18 hours after

TABLE 2

Lytic and rapid bactericidal activity of nisin against multidrug-resistant clinical isolates

| Species | Strain | Nisin (μg/ml) | Time (min) | Lysis by A590 ≧50% No. isolates/ total | Loss in viability ≧99% kill No. isolates/ total |
|---|---|---|---|---|---|
| *Streptococcus pneumoniae* | pen-r | 1.0 | 20 | 45/47 | |
| | | 1.0 | 60 | 17/18 | 16/18 |
| *Staphylococcus aureus* | MRSA | 10 | 120 | 27/30 | |
| | | 10 | 180 | 29/33 | 33/33 |
| *Staphylococcus epidermidis* | | | | | 10/10 |

TABLE 2-continued

Lytic and rapid bactericidal activity of nisin against multidrug-resistant clinical isolates

| Species | Strain | Nisin (μg/ml) | Time (min) | Lysis by A590 ≧50% No. isolates/ total | Loss in viability ≧99% kill No. isolates/ total |
|---|---|---|---|---|---|
| | MRSE | 10 | 180 | 10/10 | |
| *Enterococcus faecalis* | van-r | 10 | 240 | 10/10 | |
| | | 10–20 | 240 | 6/6 | 6/6 |
| *Enterococcus faecium* | van-r | 10 | 240 | 53/60 | |
| | | 10–20 | 240 | 12/23 | 23/23 |

TABLE 3

The efficacy of intravenous nisin towards *Staphylococcus aureus* infection in mice[a]

| Treatment | Survival |
|---|---|
| No treatment | 0/5[a] |
| Nisin 10 mg/kg | 5/5 |

[a]Untreated mice died within 18 h.

We claim:

1. A method for controlling or killing antibiotic-resistant, pathogenic bacteria responsible for disease in mammals, which comprises administering an amount of a lanthocin antimicrobial in excess of its minimal inhibitory concentration, wherein the lanthocin is selected from the group consisting of nisin, subtilin, epidermin, crallidermin and pep 5, and the bacteria are of a genus selected from the group consisting of Staphylococcus Streptococcus and Enterococcus.

2. A method according to claim 1, wherein the lanthocin is nisin.

* * * * *

UNITED STATES PATENT AND TRADEMARK OFFICE
CERTIFICATE OF CORRECTION

PATENT NO. : 5,866,539
DATED : February 2, 1999
INVENTOR(S) : Peter Blackburn and Beth P. Goldstein It is certified that error appears in the above-identified patent and that said Letters Patent is hereby corrected as shown below:

Column 6, claim 1,
Line 35, delete "crallidermin" and insert therefor -- gallidermin --.

Signed and Sealed this

Fifth Day of March, 2002

Attest:

JAMES E. ROGAN
*Attesting Officer*     *Director of the United States Patent and Trademark Office*